United States Patent
Pandey et al.

(10) Patent No.: US 10,085,718 B2
(45) Date of Patent: Oct. 2, 2018

(54) ULTRASONIC PROBE WITH A BEAM HAVING AN ULTRASONIC TRANSDUCER

(71) Applicant: NOBLE SENSORS, LLC, New York, NY (US)

(72) Inventors: Gaurav Pandey, Jersey City, NJ (US); Richard S. Koplin, New York, NY (US); Martin J. Weinberg, New Canaan, CT (US)

(73) Assignee: NOBLE SENSORS, LLC, New York, NY (US)

( * ) Notice: Subject to any disclaimer, the term of this patent is extended or adjusted under 35 U.S.C. 154(b) by 85 days.

(21) Appl. No.: 14/609,710

(22) Filed: Jan. 30, 2015

(65) Prior Publication Data

US 2016/0220228 A1 Aug. 4, 2016

(51) Int. Cl.
| | |
|---|---|
| *A61B 8/00* | (2006.01) |
| *H02K 33/00* | (2006.01) |
| *A61B 8/14* | (2006.01) |
| *A61B 8/10* | (2006.01) |

(52) U.S. Cl.
CPC .............. *A61B 8/4461* (2013.01); *A61B 8/10* (2013.01); *A61B 8/14* (2013.01); *A61B 8/4466* (2013.01); *A61B 8/54* (2013.01)

(58) Field of Classification Search
None
See application file for complete search history.

(56) References Cited

U.S. PATENT DOCUMENTS

| | | | |
|---|---|---|---|
| 3,995,409 A * | 12/1976 | Discavage | B65B 13/18 100/26 |
| 5,203,335 A | 4/1993 | Noujaim et al. | |
| 5,386,107 A * | 1/1995 | Dvorkis | G06K 7/10811 235/462.23 |
| 5,675,554 A | 10/1997 | Cole et al. | |
| 6,142,946 A | 11/2000 | Hwang et al. | |
| 2003/0220556 A1* | 11/2003 | Porat | A61B 5/0051 600/407 |
| 2005/0009197 A1* | 1/2005 | Adams | G01Q 70/08 436/164 |
| 2005/0113698 A1 | 5/2005 | Kristoffersen et al. | |
| 2008/0223292 A1* | 9/2008 | Ling | B05C 1/00 118/211 |
| 2010/0199771 A1* | 8/2010 | Koplin | A61B 8/10 73/634 |

(Continued)

FOREIGN PATENT DOCUMENTS

| | | | |
|---|---|---|---|
| EP | 0336640 | 10/1989 | |
| EP | 0336640 A2 * | 10/1989 | G10K 11/355 |

OTHER PUBLICATIONS

Patent Cooperation Treaty, International Searching Authority, Notification of Transmittal of the International Search Report and the Written Opinion of the International Searching Authority, or the Declaration, dated May 19, 2016, pp. 1-8.

(Continued)

*Primary Examiner* — Patricia Park
(74) *Attorney, Agent, or Firm* — Baker McKenzie LLP (57) ABSTRACT

An ultrasonic probe is composed of a beam having a fixed end and a free end, with an ultrasonic transceiver mounted on the free end. A driving mechanism is used to move said ultrasonic transceiver to one or more predetermined positions by applying an electromagnetic force on the beam.

28 Claims, 11 Drawing Sheets

(56) References Cited

U.S. PATENT DOCUMENTS

| | | | |
|---|---|---|---|
| 2010/0324423 A1* | 12/2010 | El-Aklouk | A61B 8/4483 600/444 |
| 2011/0122024 A1 | 5/2011 | Eidloth et al. | |
| 2011/0239383 A1* | 10/2011 | Nishiura | A61C 17/3445 15/22.1 |
| 2012/0076229 A1 | 3/2012 | Brobston et al. | |
| 2012/0236258 A1* | 9/2012 | Shrestha | A61B 3/10 351/205 |
| 2012/0248785 A1* | 10/2012 | Forman | F02B 43/10 290/1 R |
| 2013/0283918 A1 | 10/2013 | Habermehl et al. | |
| 2014/0218016 A1* | 8/2014 | Saito | G01Q 30/04 324/228 |

OTHER PUBLICATIONS

Patent Cooperation Treaty, International Searching Authority, Search History, dated Apr. 26, 2016, pp. 1-3.

* cited by examiner

ULTRASONIC PROBE WITH A BEAM HAVING AN ULTRASONIC TRANSDUCER

BACKGROUND OF THE INVENTION

A. Field of Invention

This application pertains to a diagnostic ultrasonic scanning probe having a cantilevered or a hinged beam supporting an ultrasonic generator/sensor, as well as an excitation and control circuit for controlling linearly the lateral movement of the beam. Optionally the control circuit is integrated with the controls for the transducer.

B. Description of the Prior Art

Diagnostic ophthalmic ultrasonic probes make use of well-known, safe diagnostic medical imaging techniques in which ultrasound waves are used to create images representative of a patient's eyes. Ultrasonic probes are advantageous in that they are noninvasive diagnostic tools that provide images virtually instantaneously and can be used for the evaluation of various ophthalmic disorders.

Ophthalmic ultrasound probes use pulse-echo system. A series of emitted pulses at pre-determined ultrasound frequency are emitted by the probe that is in contact with a patient's lid or eye. At every acoustic interface, some of the echoes are reflected back to the transducer, indicating a change in tissue density. The echoes returned to the probe are converted back into an electrical signal and processed as ultrasound images. Typically, ophthalmic ultrasound machines may use frequencies in the range of 6 to 80 MHz, compared with 2 to 6 MHz typically used in other fields of diagnostic ultrasound. Each pulse is followed by a brief pause (microseconds) during which echoes of the pulses are received and processed and the resulting images are presented on the display screen.

The A-scan, B-scan and ultrasound biomicroscopy are the most commonly used ophthalmic ultrasound techniques. The A-scan technique results in a one-dimensional display of echo strength over time (time delay). The vertical spikes are generated that correspond to the reflected echo intensity and are typically demonstrated as a function of time. The technique commonly uses a frequency range of about 6 to 12 MHz and is mainly used for documenting axial eye length measurements of the eye: to measure the distance between the anterior cornea and retina. This distance is used to calculate the appropriate power of an intraocular lens implant used at cataract surgery.

The B-scan technique generates a two dimensional image of the echoes along both a horizontal and vertical axis. It is an important tool for the clinical assessment of various ocular and orbital diseases. In situations in which normal examinations are not possible, such as lid problems, corneal opacities dense cataracts, or vitreous opacities, diagnostic B-scan ultrasound can accurately image intraocular structures and give valuable information on the status of the lens, retina, and other areas of anatomy.

Ultrasound biomicroscopy is an ultrasonic technique that uses frequencies from 35 to 80 MHz for the acoustic evaluation of anterior segment of the eye. Higher frequency use results in more detailed imaging of the anterior segment of the eye.

Historically ultrasonic probes have been utilized with a water stand-off and the examiner manipulating a transducer free hand. This technique was found to be unwieldy and time consuming.

Currently, most B-scan diagnostic ultrasonic probes are in a self-contained cylindrical package—with a small amount of water or other fluid stand-off built into the device around the transducer element. The self-contained device may be positioned directly on the eye or lid by the physician and moved about without injuring the eye. Using these devices the probe—typically, a single transducer—is moved mechanically in an arc scan across the eye, and at regular intervals, an ultrasound pulse is directed into the eye and the resulting echoes are received by the same transducer and analyzed.

The present state the art utilizes several motorized mechanical parts to provide this mechanical movement. In this design the transducer is typically driven in a sector or arc scan (although other scan configurations are possible) inside the enclosed water bath. Water or some other fluid is required in these systems since air results in total internal reflection and the ultrasonic beam fails to exit the probe. Moreover, the cabling between the probe and the mechanical device requires a coaxial cable of some design, carrying signals to and from the transducer, as well as leads carrying the drive current to the electric motor and the signal from the position sensor. These cables often fail with continued use due to mechanical fatigue as well as exposure to elevated temperatures. The probe is made compact by having the necessary drive components built into and closely around the rocking transducer assembly.

Mechanical scanning is currently the industry standard in ophthalmic systems (including systems using combined A and B-scan capabilities). Despite the disadvantages associated with moving parts, such as wear and tear, vibration, and resultant heat the level of acoustic noise associated with these scanners was considered tolerable using insulation and software filters.

Co-pending patent application US 20120236358 describes an ultrasonic probe with resonant beam vibrating at its natural mechanical frequency of resonance in a manner similar to a tuning fork to move an ultrasonic transceiver.

SUMMARY OF THE INVENTION

The present inventors have developed a low cost ultrasonic probe particularly suited for ophthalmic applications. The present device uses an electromagnetically actuated beam. It has been found that this configuration results in a probe that is low cost, provides accurate results, and requires relatively minimal electronic control and the capability of mounting both B-scan and UBM probes on the same actuator.

In one embodiment, the beam is a cantilevered beam fixed to a support structure. In another embodiment, the beam is provided with a hinge supporting the beam within the housing. In another embodiment, the beam is configured to move along a linear path.

At least a portion of the beam is made of a magnetic or magnetizable material and an electromagnetic control circuit is used to drive the beam, or at least its free end along a predetermined angular path. An ultrasonic transceiver is mounted on the end of the beam and is driven by the beam along said path to scan the eye of a patient. Preferably, in one embodiment, one or more stationary electromagnetic coils interact with one or more permanent magnets mounted on the beam to generate a magnetic force on the beam thereby moving the beam along a predetermined path. Alternatively, the one or more electromagnetic coils are attached to the beam and the permanent magnet(s) are stationary.

In one embodiment, the beam is supported in a manner that allows the whole beam is allowed to move in a direction preferably perpendicularly to a longitudinal axis of the beam. Magnetic or other means are used to reciprocate the beam in a predetermined motion thereby enabling the ultrasonic transducer to scan a patient's eye.

In one embodiment, the control circuit includes a variable current generator and one or more coils receiving current from the current generator and applying a predetermined force on the beam thereby reciprocating the beam along the angular path.

DETAILED DESCRIPTION OF THE INVENTION

The present inventors have developed and experimentally tested an electromagnetic positioning mechanism for ophthalmic B-scan probe. The probe can be easily adapted to perform A-scan and UBM probes, as well as many other ultrasonic probes as well.

Figure 1:
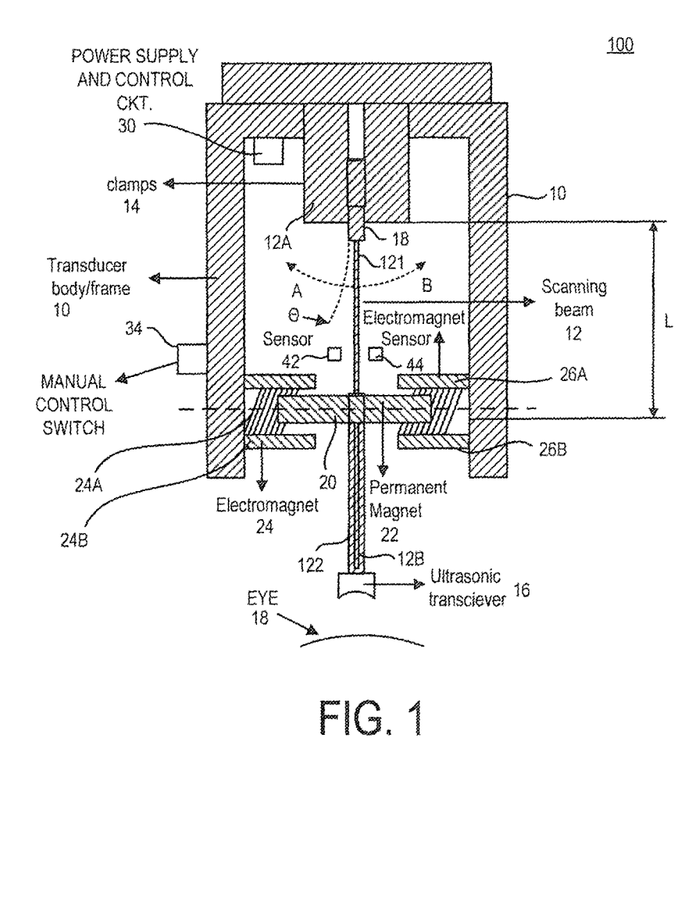
FIG. 1 shows somewhat diagrammatic side sectional view of an ultrasonic probe constructed in accordance with this invention.

As shown in FIG. 1, a probe 100 constructed in accordance with this invention includes a housing 10 which includes all the elements of the probe. Preferably, the housing 10 is preferably sized and shaped so that it can fit into the hand of a user. The housing 10 includes a beam 12 having an end 12A supported within the housing 10 by a pair of claims 14. The other end 12B of the beam supports an ultrasonic transceiver 16. As discussed below, the transceiver typically includes an ultrasonic pulse generator and a sensor sensing echoes from a target, such as an eye 18. In one embodiment, the beam 12 is made of steel and consists of two sections 121 and 122 solidly and collinearly attached to each other. Section 121 has generally rectangular cross section of about 1" long by 0.5" wide by 0.05" thick. The rectangular beam section 121 is followed or attached to cylindrical section 122 (holding the ultrasonic sensor 16).

Section 122 has of 0.25" diameter and 2.5" length. The beam 12 is somewhat flexible so that when a force is applied on it, it can flex by an angle in either directions A or B. In normal use, the beam is forced to flex angularly in a reciprocating motion and a predetermined driven frequency normal for ultrasonic probes. For example, this frequency may be about 10-20 Hz. The deflection of the beam is sufficient to move the transceiver 16 by ±5 cm. The beam 12 is constructed and arranged so that has a much higher natural resonant frequency (e.g., several orders of magnitude) than the driven frequency. For a cantilevered steel beam of 1 inch length and 0.05" thickness, the resonant frequency is about 500 Hz. As a result, the movement of the beam is not affected by external forces as the probe is being handled by a physician, for example during a normal image gathering process. In the prototype built by the inventors, clamps 14 selectively open and close to allow the beam 12 to be removed and replaced by a different beam having different physical characteristics (such as its resonant frequency) or different transducer 16. Alternatively, the beam 12 and transducer 16 can be configured so that the transducer can be mounted at will, dismounted from the beam 12 and replaced with another transducer, as desired.

A sheath 18 may be provided between the beam 12 and the clamps (or other structure used to support the beam 12 within the housing 10 to isolate the beam 12 mechanically and to prevent or at least reduce the vibration of the beam 12 and transducer 16 from being transmitted to the housing 10.

Also mounted on the beam 12 are two permanent magnets 20, 22. These magnets are preferably strong magnets, made, for example, of rare earths such as neodymium, so that they can generate strong magnetic fields.

Mounted within the housing 10 there are also two electromagnets 24, 26. The electromagnets typically include coils 24A, 26A disposed on hollow shafts 24B, 26B. The electromagnets are excited by power from a power supply and control circuit 30. The magnets 20, 22 and electromagnets 24, 26 are constructed and arranged to apply a deflecting force on the beam alternately in directions A and B, as discussed in more detail below.

Figure 1A:
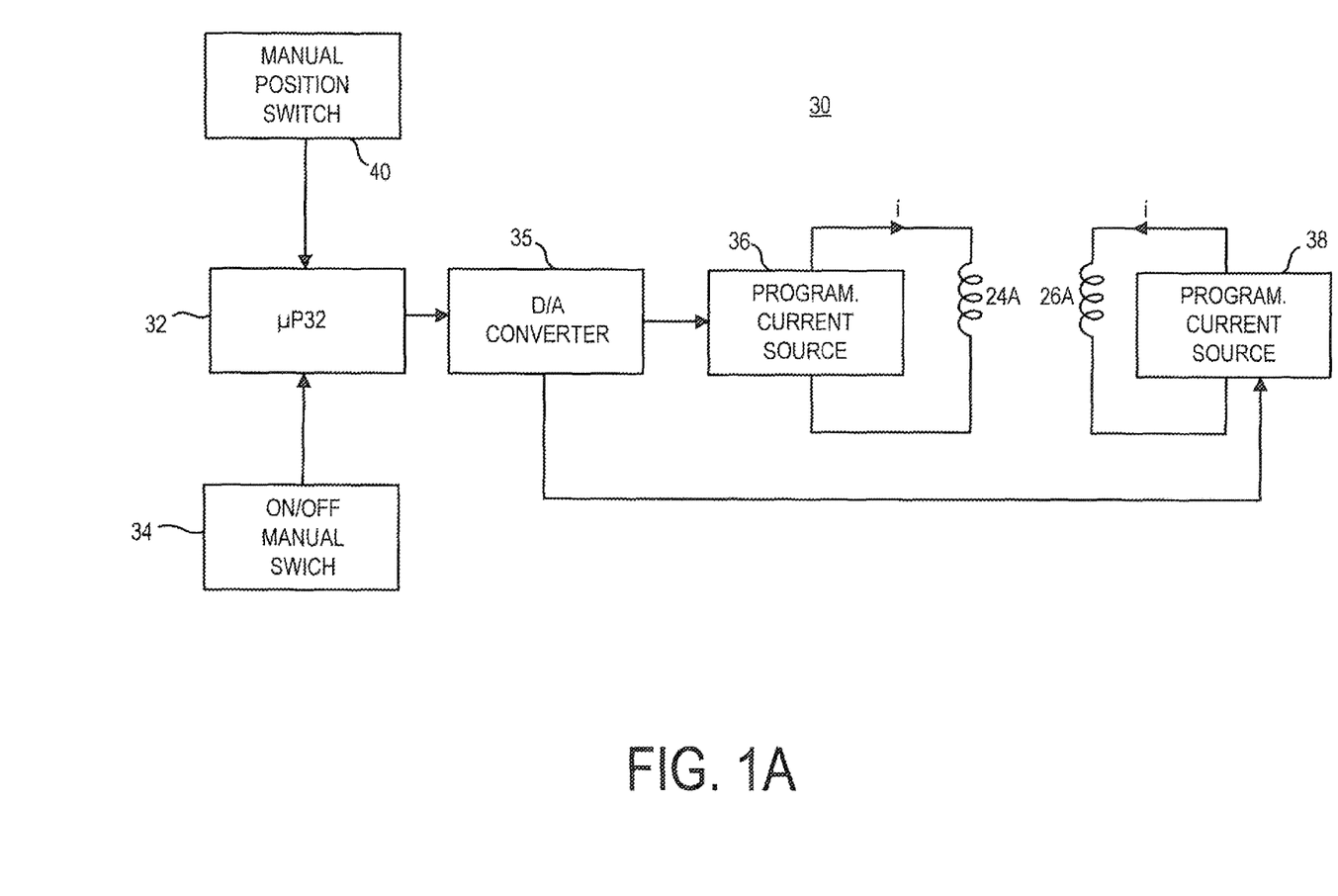
FIG. 1A shows a block diagram of the components of probe of FIG. 1 used to position its ultrasonic transceiver.

A somewhat simplified circuit diagram of the power and control circuit 30 is shown in FIG. 1A. The circuit 30 receives power either from a battery (not shown) or from an AC power source (not shown) and it includes a microprocessor 32. The microprocessor 32 receives inputs from a manual on/off switch 34. The circuit 30 further includes a digital-to-analog converter 35 that provides analog control signals to two programmable current generators 36, 38. (The digital-to-analog converter 35 could be incorporated into the microprocessor 32. Alternatively, the current generators 36, 38 may be configured to respond to digital control signals, in which case the D/A converter 35 is omitted). The current generators 36, 38 generate respective current for coils 24A, 24B of electromagnets 24A, 26 respectively.

The magnetic fields generated by the coils 24A, 26A are uniform and have an intensity given by equation (1) below:

$$B = \mu_0 n i \quad (1)$$

where $\mu_0$ is the magnetic permeability of air, n is the number of turns per unit length and i is the current through the electromagnet coil. The force experienced by each of the respective permanent magnets 20, 22 in the magnetic field of the electromagnets is given by:

$$F = kB \quad (2)$$

where k is a constant dependent on the strength and length of the permanent magnet and B is the magnetic field of the solenoid. Hence the force on the cantilever beam 12 is a linear function of current through the electromagnet coil. The device is very stable and does not need a PID control system. As a result, the probe is low cost and stable. If two permanent and two electromagnets are used, as shown in FIG. 1, the force on the cantilevered scanning beam is doubled. The angular deflection of the cantilever is given by equation (3) below:

$$\theta = kBL^2/EI \qquad (3)$$

Where L is the distance between the center of the electromagnets and the clamps supporting beam 12, as shown in FIG. 1 and I is the average moment of inertia of the beam 12. Hence by just changing the coil current i, the angle of deflection of the cantilever can be varied. Importantly, this angle can be varied linearly, making the control system simple and straight forward.

After the device 10 is assembled it can be calibrated (e.g., the parameters of the equations above can be determined) by generating a current through each of the coils and measuring the resulting deflection angle θ. Alternatively, sensors such as Hall effect sensors may be placed near the beam, a known current can be applied to the coils and the device can be calibrated using the outputs of the sensors.

It is believed that for most devices, the control circuit shown in FIG. 1A is sufficient. Moreover, the device shown in FIGS. 1 and 1A does not require stepper motors or complicated mechanical drive trains. The device is able to provide the angular reciprocating motion necessary for various ophthalmic applications.

The device 100 operates as follows. The microprocessor 32 is programmed to reciprocate transceiver 16 by about ±5 cm and a frequency of 10 Hz using a triangular, sinusoidal or other similar wave shapes. The physician positions the device as shown in FIG. 1 with the transceiver 16 pointed at the eye, and he then activates an an/off manual switch 34 on housing 12. The position of the switch 34 is sensed by the microprocessor 32 which then sends appropriate control signals to the programmable current generators 36, 38 to generate respective current wave shapes. As discussed above, since the circuit in FIG. 1A is linear, the microprocessor 34 and generators 36, 38 cooperate to generate to vary current i (which is a DC current) linearly to follow the desired waveshapes. In response, the beam 12 reciprocates angularly moving the transceiver 16 back and forth and allowing the transceiver 16 to scan the eye 18.

In some instances, it may be desirable to position the transducer 16 to a predetermined angle. For this situation, a manual switch 40. When this switch is activated, the microprocessor generates a positioning signal to the current generators 36, 38 thereby causing the beam to move the transceiver 16 to a predetermined position or angle.

Figure 2:
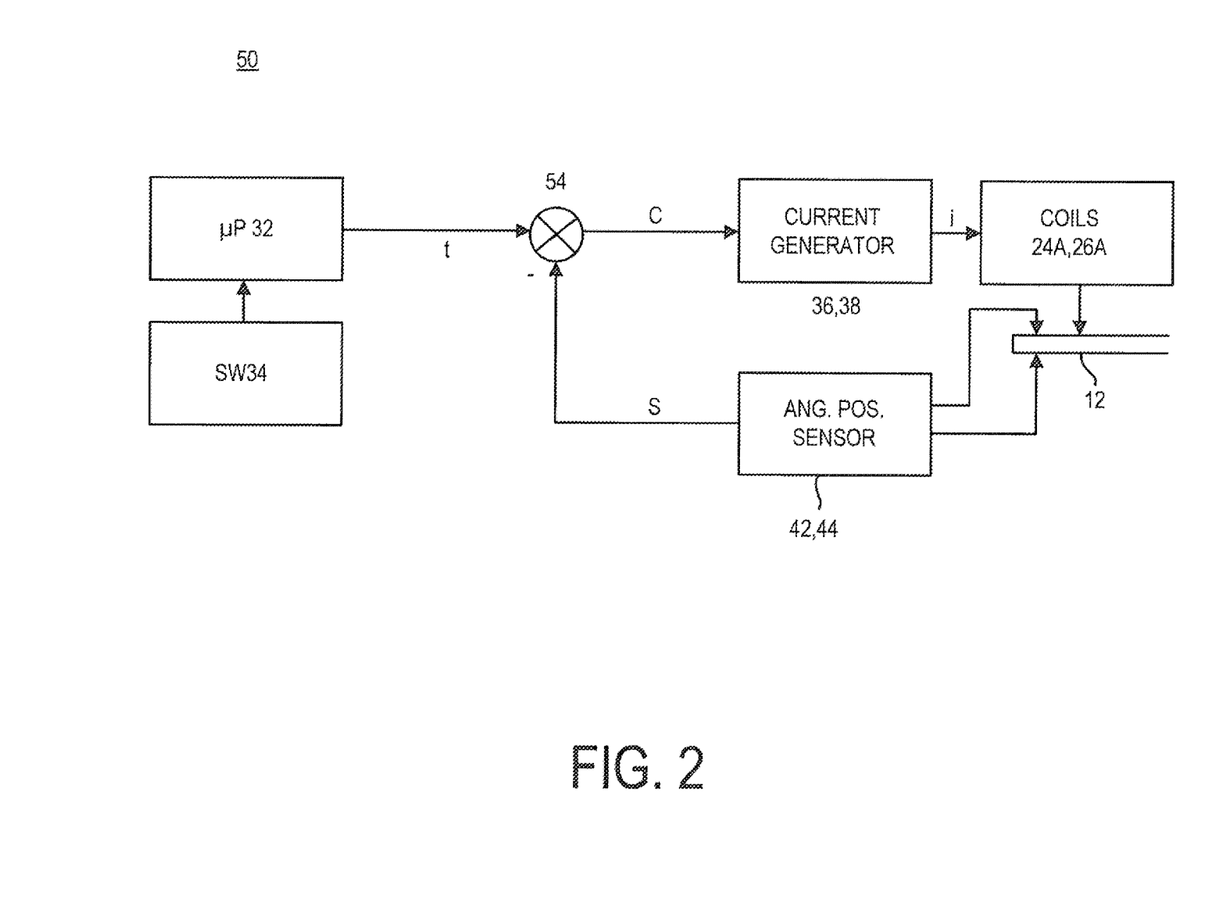
FIG. 2 shows an alternate embodiment with one or more position sensors.

For some applications, because of various internal effects, the movement of the transceiver 16 may not be precise enough. For these applications, a modified control circuit with feedback control loop may be used. For example, the device 100 can be provided with either a single sensor 42 or a pair of sensors 42, 44 disposed symmetrically on the two sides of the beam 12. The modified control circuit 50 is shown in FIG. 2. The target signal t is sent from the microprocessor 32 to a summer 54. The output of the summer c is fed to current generators 36, 38. The generators generate a current i that is fed to the coils 24A, 26A. The coils deflect the beam and the actual position of the beam 12 is sensed by sensors 42, 44 and the sensed signals s are fed back to the summer 54. The circuit 50 can be implemented with a single sensor, with two sensors, in which case, one of the sensors is used when the beam moves in direction A and the other sensor is used when the beam moves in direction B.

Figure 3A:
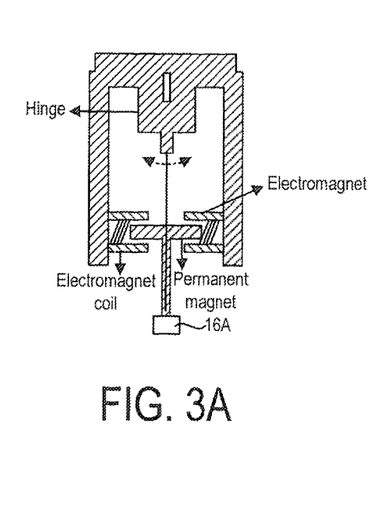
FIG. 3A, 3B show somewhat diagrammatic front and side views of a probe with several discrete ultrasonic transceivers.
Figure 3B:
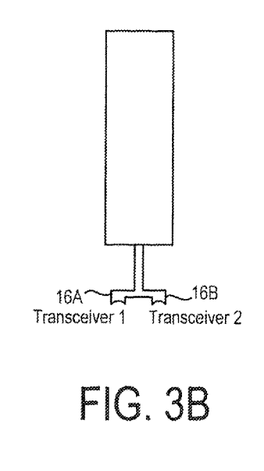

Preferably, the beam 12 and the transceiver 16 are constructed so that the transceiver can be easily removed from the beam end 12B and changed to a different transceiver. In one embodiment, the beam end 12B is provided with two transceivers 16A, 16B arranged side by side, as seen in FIGS. 3A and 3B, with two transceivers being separated by a distance of that can be 2-3 times the cross-sectional diameter of transceivers. The two transceivers 16A, 16B can be operating at different frequencies, for example, one being configured to perform A scans and the other being configured to perform B scans. Thus, the device 100 is 'modular' in nature as it allows for both high and low frequency ultrasound probes to be mounted on the same device. The low frequency ultrasound transceiver is used for a generic ophthalmic scan and the high frequency transceiver is used for ultrasonic bio microscopy or UBM. This is a major improvement over the present state-of-art probes which have either high frequency or low frequency transducers.

Figure 3C:
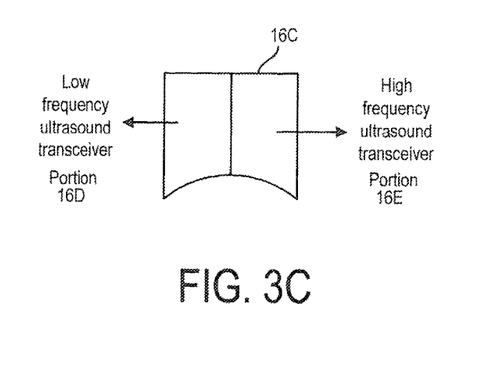
FIG. 3C shows an enlarged side view of a multi-mode ultrasonic transceiver.

Alternately, a transceiver 16C can be provided which has two transceiver portions 16D and 16E, as shown in FIG. 3C. One transceiver portion is operates at a high frequency and the other portion can be operating at a low frequency.

Figure 4:
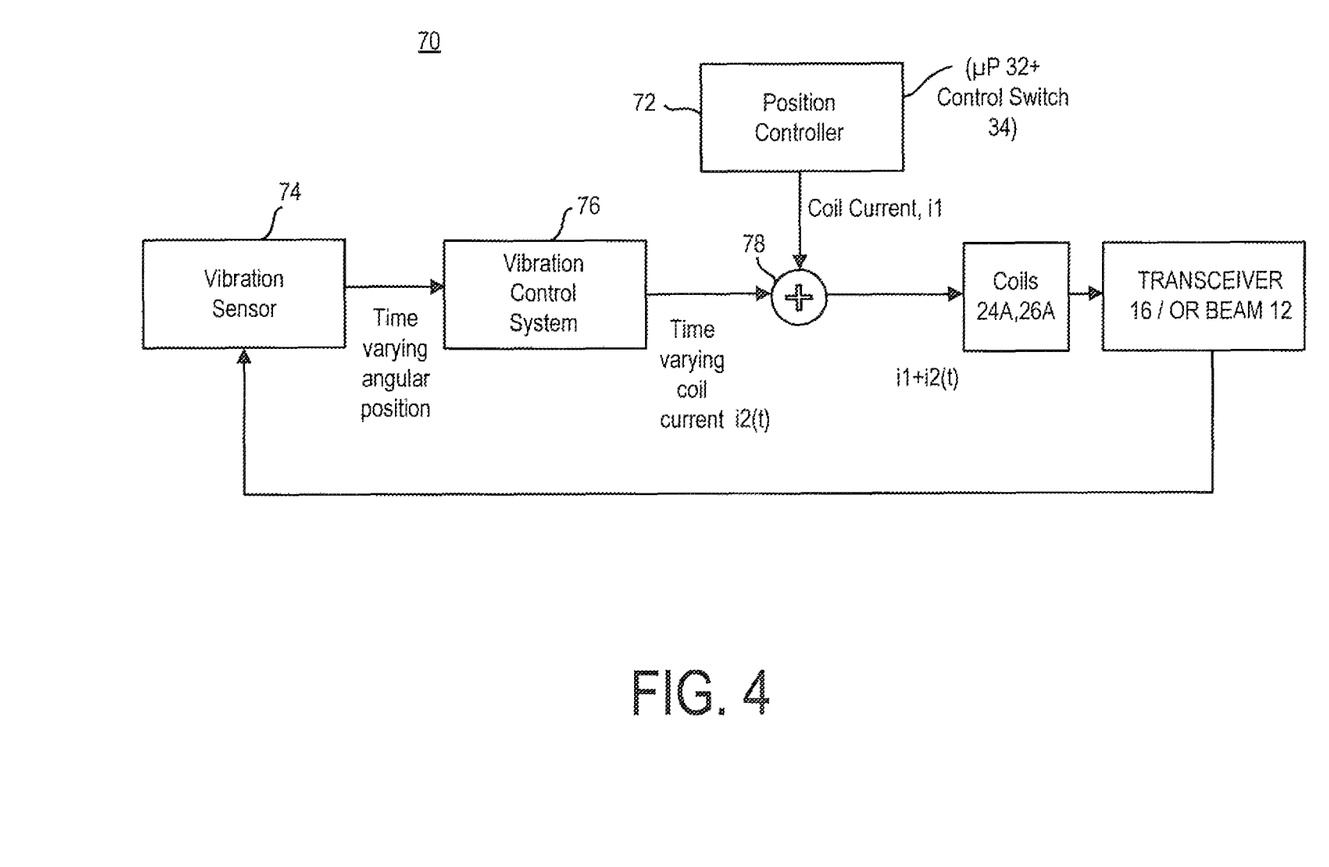
FIG. 4 shows a block diagram of another embodiment with the invention with vibration compensation.

As previously indicated, the inventors believe that the device 100 as discussed above is very robust and can operate in satisfactory manner even in the presence of external vibrations. However, if it is desired to eliminate any interference from such vibrations, an active control system can be used, instead of the control systems from FIG. 1A or 2. Such an active control system 70 is shown in FIG. 4 and it includes a position controller 72, a vibration sensor 74, a vibration controller 76 and a summer 78.

The position controller 72 is used to determine the desired position of the transceiver 16 and/or beam 12 as a function of time. The position controller 72 may include, for example, microprocessor 32 and the manual control switch 34. The position controller generates a current $i1(t)$.

The undesired vibration is detected by a vibration sensor 74. This sensor may be positioned to sense a vibration in the angular position of the transceiver 16, or beam 12. Alternatively, the sensor 74 may sense a vibration of another element of the device 100, such as its housing 10, etc. The output of vibration sensor 74 is presented to a vibration controller 76. The vibration controller determines how the beam 12 should change its angular position to cancel the vibration detected by the sensor 74. The system 76 then generates a second time varying current $i2(t)$. The two signals $i1(t)$ and $i2(t)$ are added algebraically by summer 78 and provided to the coils 24A, 26A.

In other words the vibration control system can simply superimpose a time-dependent current to the electromagnets in addition to the actuation voltage. The vibration control system may also use piezoelectric or otherwise active elements mounted on the probe cantilever to sense vibrations at various locations within or outside the housing 10.

Figure 5:
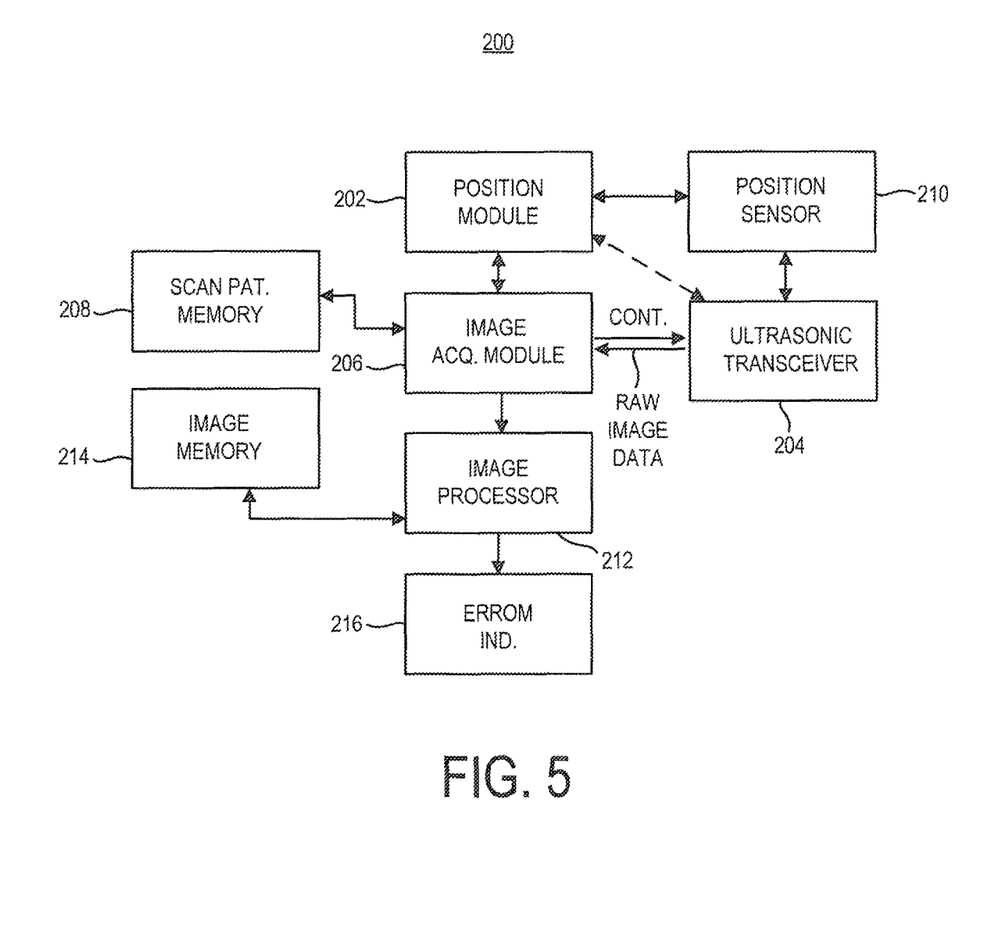
FIG. 5 shows a block diagram of a unified control system with interactive components for both positioning and the transceivers and acquiring ultrasonic images.

In the embodiments described so far, the control system used for positioning the ultrasonic transceiver(s) are separate from, and operate independently of the control system used to operate the transceivers themselves. However, there may be several advantages in unifying these two systems to make them less expensive, more energy efficient and obtain more accurate, higher resolution images. One such unified system is shown in FIG. 5. This unified system 200 can include two processing modules: a positioning module 202 for positioning an ultrasonic transceiver 204 and an image acquisition module 206 for activating the transceiver 204 as required, and to collect the resulting imaging data.

The unified system 200 operates as follows. A scanning pattern memory 205 is used to store scanning patterns for different kinds of scanning techniques discussed above. For example, these patterns may define the scanning range required for the ultrasonic transducer 204, the duration and/or intensity of ultrasonic pulses, the various positions of the transducer for each pulse, etc. When the image acquisition module 206 receives a request for an image, it first retrieves an appropriate scanning pattern from memory 208. Then the module 206 sends one or more commands to positioning module 202. The positioning module 202 is configured as described above and in FIGS. 1-4 to position the transceiver 204 to a position dictated by the pattern from memory 208. As discussed above, the position module 202 may be accurate enough to achieve this operation without any sensory feedback. Alternatively, one or more position sensors 210 may be used to determine that the transceiver 204 has reached the required position.

Once the required position is reached, the image acquisition module 206 sends a command to the transceiver 204 to start the image acquisition process. As part of this process, the transceiver sends one or ultrasonic pulses toward the eye of patient. Echoes from these pulses are sensed within the transceiver and are transmitted as raw image data back to the image acquisition module 206. The module 206 sends this raw data to an image processor 212. The image processor either stores this data in an image memory 214, or performs some processing on the raw data and the processed data is stored in memory 214. The transceiver 204 is moved to the next position and a new set of raw data is collected until the whole eye is scanned, the raw data is processed and the desired image is obtained and stored in image memory 214.

In one embodiment, either during or after the image processing, the processor 212 checks the raw data to determine if the raw data is acceptable. Of the raw data or the resulting image is not acceptable, for example, because of some external causes such as vibrations, an error indication is activated by module 216 to indicate that this event. In this case, the whole process may be repeated.

The system 200 shown as including several different modules, such as modules 202, 206 212 and 216 for the sake of clarity. However it should be understood that the invention could be implemented with all or some of these modules being incorporated into a single microprocessor.

Moreover, the system may be configured to receive either one of several ultrasonic transceivers 204, each transceiver being configured to perform a particular scanning technique. Alternatively, two transceivers may be mounted on the same beam and used as discussed above.

Figure 6:
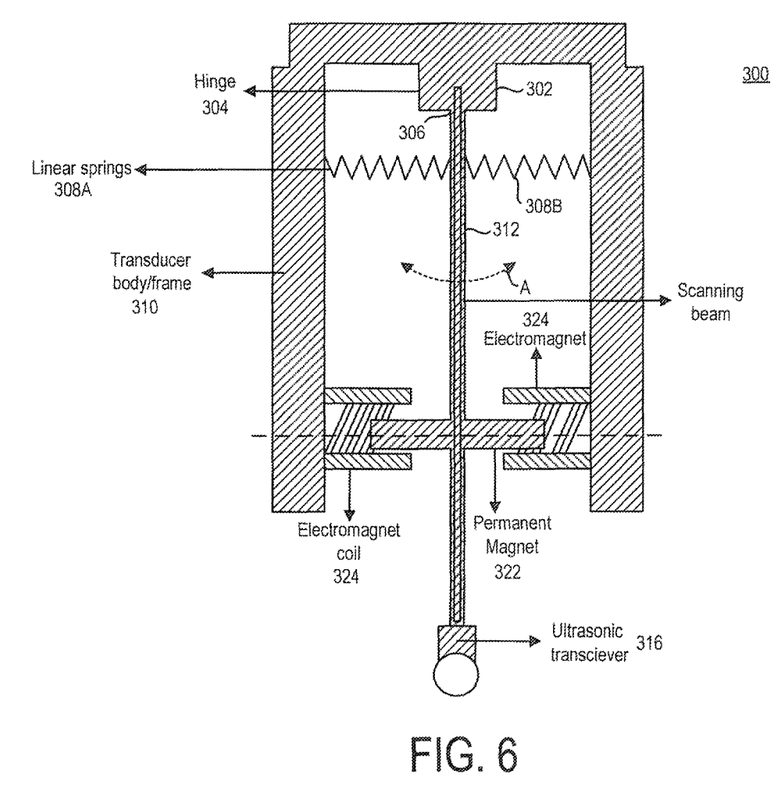
FIG. 6 shows an alternate embodiment showing a side sectional, somewhat diagrammatic view of a transducer with a hingedly supported beam biased by two springs.
Figure 7:
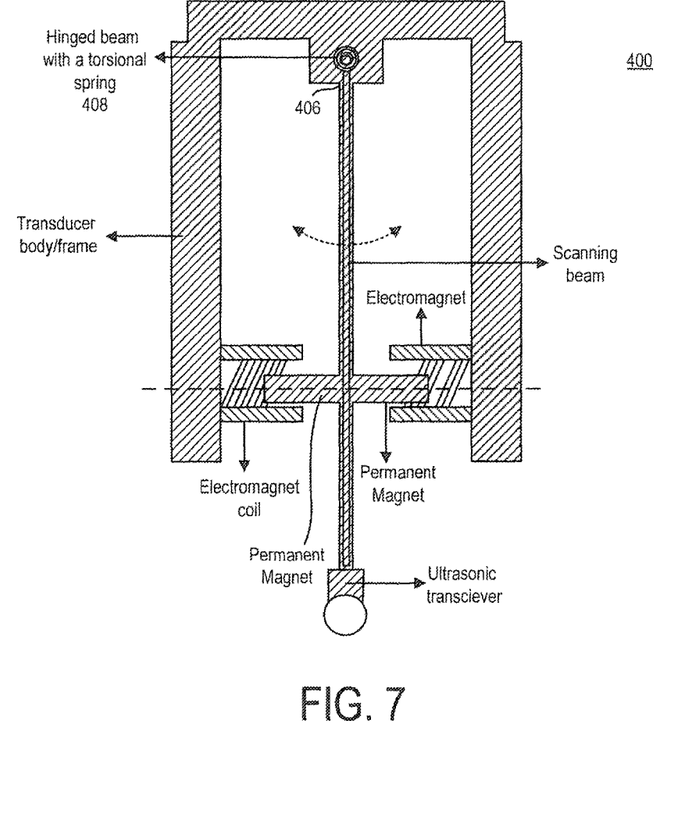
FIG. 7 shows an alternate embodiment with a side sectional, somewhat diagrammatic view of a transducer with a hinged beam biased by a single coil springs.

In alternate embodiments of FIGS. 6 and 7, a probe is shown in which the cantilevered beam of the previous embodiments is replaced by a hinged beam. Referring to FIG. 6, probe 300 includes a housing or frame 310 including a post 302. A beam 312 is supported on this post 302 by a hinge 304 that allows the beam 312 to pivot in an angular motion represented by arrow A around axis 306. A pair of springs 308A, 308B bias the beam 312 toward a normal or neutral position which is preferably collinear with a longitudinal axis of the housing 310. Magnets 322 are supported on beam 312 and cooperate with electromagnetic coils 324 to control the angular movement of the beam 312. This movement is very similar to the movement of beam 12 but instead of bending along its length, beam 312 pivots about axis 306 and moves transceiver 316.

In another alternate embodiment shown in FIG. 7, beam 412 pivots about an axis 406 and is maintained in a neutral position by a coil-type spring 408. Probe 400 operates essentially in the same manner as probe 300 of FIG. 6.

Figure 8:
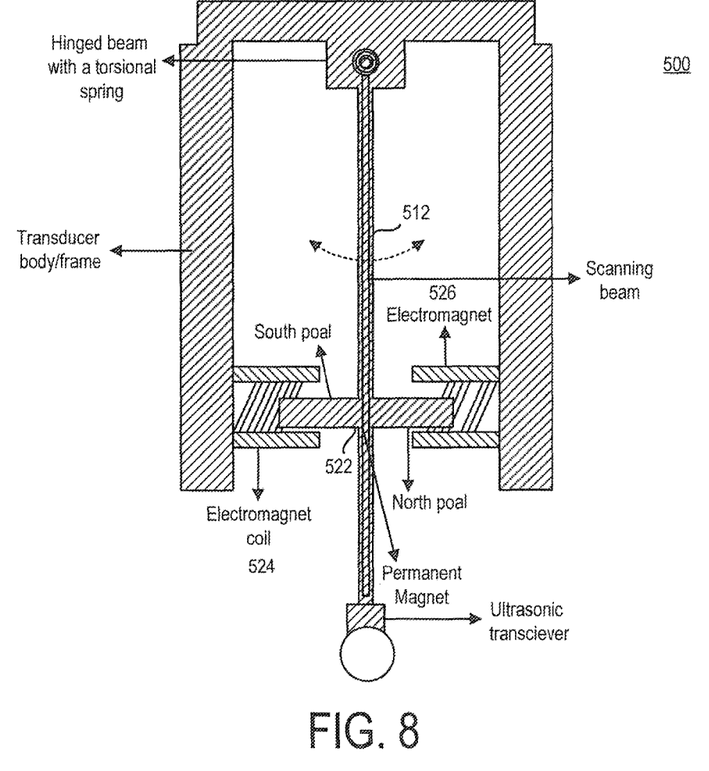
FIG. 8 shows another alternate embodiment of the invention in which a single magnet is provided on the beam rather than dual magnets.

In the embodiment of FIG. 1 (and all subsequent embodiments described until now) two magnets 20, 22 are mounted on the beam 12. The magnets are arranged and constructed so that one of their poles is disposed within one of the respective coils 24A, 26A of the electromagnets 24, 26. In the embodiment of FIG. 8, an alternate arrangement of a probe 500 is shown. The system includes a beam 512 with electromagnets 524, 526. However, instead of two permanent magnets, the beam carries a single permanent magnet 522 with a south pole and a north pole. The south pole extends into the coil of electromagnet 524 and the north pole extends into electromagnet 526 as shown. The operation of the device 500 is similar to the operation of the devices disclosed above.

Figure 9:
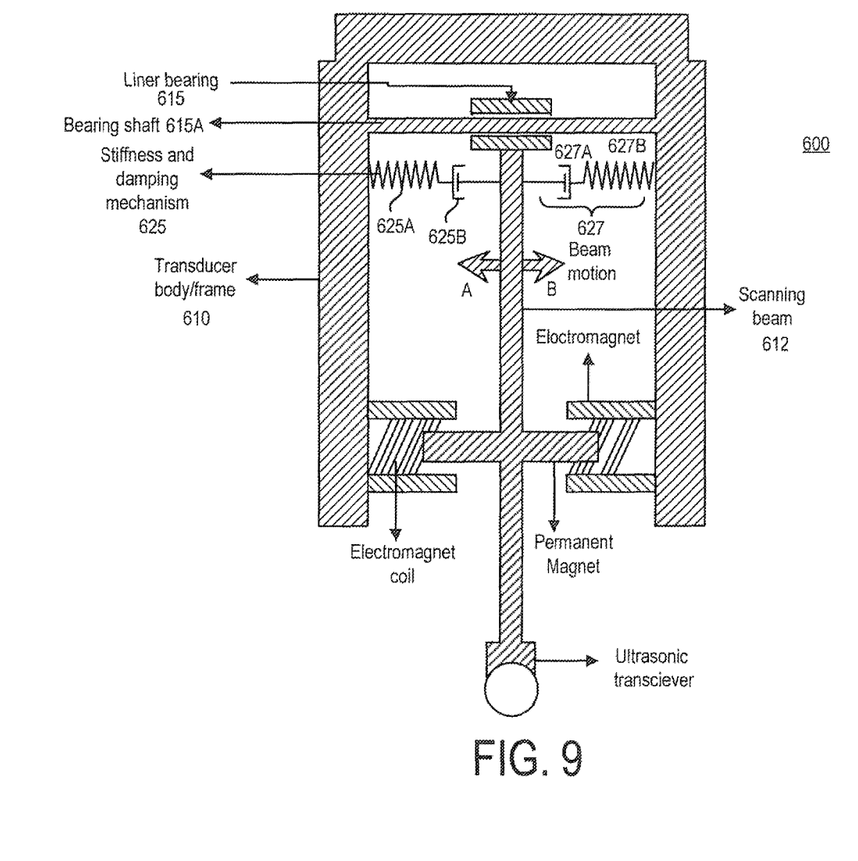
FIG. 9 shows yet another embodiment of the invention in which the beam is reciprocated laterally in a linear rather than angular motion.

In the embodiments of FIGS. 1 and 8 probes are shown having beams 12, 512 that are selectively deflected or pivoted, but in either case the respective ends of the beams are moved angularly along a predetermined path. FIG. 9 shows yet another embodiment. In this embodiment, a probe 600 includes a beam 612 having one end 612A mounted on a transversal rod or bearing shaft 613 by a linear bearing 615. The linear bearing 615 is arranged and constructed to allow the beam to move laterally in either direction linearly on shaft 613, perpendicularly to the longitudinal axis of the beam 612. The bearing 615 insures that there is very little friction opposing the motion of the beam. The motion of the beam is indicated by arrows C, D. Shaft 613 is attached to the frame 610 and is stationary.

Stiffening mechanisms 621, 623 are used to control the movement of the beam 612. For example, the mechanisms may include spring 625A, 625B used to bias the beam 612 toward a predetermined neutral position. Damping devices 627A, 6278 are used to dampen the movement of the beam to insure the beam 612 does not move too fast and overshoot a predetermined target or desired position. For the sake of simplicity, springs 625A, 627A are shown as coil springs but it should be understood that other kinds biasing devices may be used as well. Similarly, devices 625B, 6273 are shown as dashpots, it being understood that other kinds of damping devices may be used as well. Moreover, the stiffening mechanisms 621, 623 may be used with the other embodiments to control the movement of a pivoting or flexing beam (shown in the other Figures) and not just the translating beam shown in FIG. 9.

Figure 10:
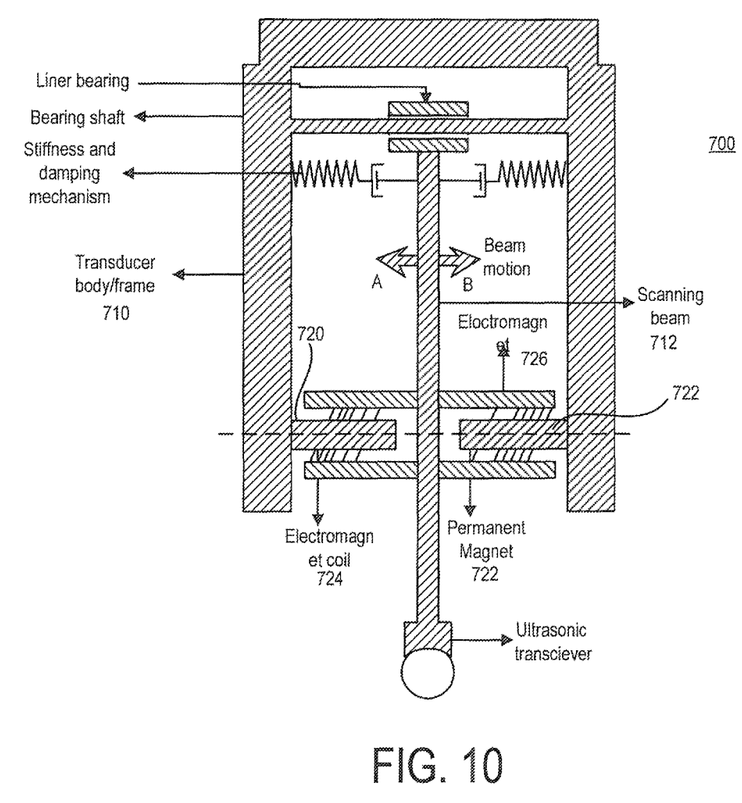
FIG. 10 shows another embodiment with the magnets being stationary and the electromagnetic coils being attached to the beam.

FIG. 10 shows yet another embodiment of the invention. In this embodiment, a probe 700 has two permanent magnets 720, 722 that are stationary and are supported by standard means on frame 710. Electromagnets 724, 726 are mounted on the frame 712. As before the magnets and electromagnets cooperate to generate magnetic forces for moving the beam 712 as described.

Of course, the arrangement of permanent magnets 720, 722 and electromagnets 724, 726 can be used in all the other embodiments described above as well.

Numerous modifications may be made to this invention without departing from its scope as defined in the appended claims.

We claim:

1. An ultrasonic probe for performing a scan on the eye of a patient comprising:
  an ultrasonic transceiver assembly configured to generate sound pulses;

a beam having a first end coupled to the ultrasonic transducer assembly and a second end coupled to a support point;
a first electromagnetic coil disposed at a first side of the beam;
a first permanent magnet disposed at the first side of the beam and extending at least partially into the first electromagnetic coil;
a second electromagnetic coil disposed as a second side of the beam;
a second permanent magnet disposed at the second side of the beam and extending at least partially into the second electromagnetic coil; and
a driving mechanism configured to drive the first and second electromagnetic coils at a range of driving frequencies from a lowest driving frequency to a highest driving frequency, wherein
the beam has a natural resonant frequency at least an order of magnitude higher than the highest driving frequency.

2. The probe of claim 1, further comprising a controller configured to cause the driving mechanism to drive the beam in response to control signals.

3. The probe of claim 1, wherein at least one of the first and second permanent magnets is disposed on the beam.

4. The probe of claim 1, wherein s one of the first permanent magnet and the first electromagnetic coil is stationary and the other of the first permanent magnet and the first electromagnetic coil is disposed on the beam.

5. The probe of claim 4, wherein the first permanent magnet is stationary.

6. The probe of claim 4, wherein the first electromagnetic coil is stationary.

7. The probe of claim 1, wherein the first side of the beam is opposite to the second side of the beam.

8. The probe of claim 7, wherein the driving mechanism is configured to drive the first and second electromagnetic coils simultaneously.

9. The probe of claim 7, wherein the driving mechanism is configured to drive the first and second electromagnetic coils sequentially.

10. The probe of claim 7, further comprising first and second current generators configured to respectively supply current to the first and second electromagnetic coils.

11. The probe of claim 10, wherein the first and second current generators are respectively configured to generate direct current.

12. The probe of claim 1, wherein the ultrasonic transducer assembly includes a first transducer configured to operate in a first mode and a second transducer configured to operate in a second mode.

13. The probe of claim 1, wherein the driving mechanism is configured to drive the beam in a reciprocating angular motion.

14. The probe of claim 1, wherein the driving mechanism is configured to drive the beam in a reciprocating linear motion.

15. An ultrasonic probe for performing a scan on the eye of a patient comprising:
a housing;
a transceiver assembly configured to generate sound pulses and detect reflected sound pulses from an eye;
a beam having a first end coupled to the transceiver and a second end supported by the housing;
a first electromagnetic coil disposed at a first side of the beam;
a first permanent magnet disposed at the first side of the beam and extending at least partially into the first electromagnetic coil;
a second electromagnetic coil disposed as a second side of the beam;
a second permanent magnet disposed at the second side of the beam and extending at least partially into the second electromagnetic coil; and
a positioning mechanism configured to position the first end of the beam by driving at least one of the first and second electromagnetic coils at a range of driving frequencies from a lowest driving frequency to a highest driving frequency generate an electromagnetic field in the respective at least one coil, wherein
the beam has a natural resonant frequency at least an order of magnitude higher than the highest driving frequency.

16. The probe of claim 15, wherein
the beam includes a cantilevered beam that includes a first beam portion and a second beam portion,
the second beam portion is coupled to the housing, and
the positioning mechanism is configured to cause the beam to bend and position the transceiver assembly.

17. The probe of claim 15, further comprising a hinge coupled to the second end of the beam, wherein the positioning mechanism is configured to cause the whole beam to pivot about the hinge.

18. The probe of claim 17, wherein the positioning mechanism includes a first spring disposed in the housing and configured to bias the beam toward a neutral position.

19. The probe of claim 18, further comprising a second spring disposed in the housing, the first and second springs configured to apply spring forces on the beam in different directions.

20. The probe of claim 15, wherein at least one of the first and second electromagnetic coils is stationary.

21. The probe of claim 15, wherein the positioning mechanism is configured to move the beam along an angular path.

22. The probe of claim 15, wherein the positioning mechanism is configured to move the beam along a linear path.

23. The probe of claim 15, further comprising a linear bearing coupled to the housing and supporting the second end of the beam.

24. The probe of claim 15, wherein the positioning mechanism is configured to hold the beam at a position forming a non-zero angle relative to a position of the beam when the electromagnetic field is not generated.

25. The probe of claim 15, wherein the positioning mechanism is configured to supply DC power to at least one of the first and second electromagnetic coils to cause the transceiver to move along a desired path.

26. The probe of claim 25, further comprising a processor programmed to determine a current waveshape that when supplied to at least one of the first and second electromagnetic coils causes the transceiver to move along the desired path.

27. The probe of claim 1, further comprising a first sensor configured to detect a position of the beam, the first sensor being disposed at the first side of the beam.

28. The probe of claim 1, further comprising a second sensor configured to detect a position of the beam, the second sensor being disposed at the second side of the beam.

* * * * *